United States Patent [19]

Collins

[11] Patent Number: 5,063,908

[45] Date of Patent: Nov. 12, 1991

[54] ADAPTER FOR CERVICAL SPECULUM

[76] Inventor: Jason H. Collins, 1344 Covington Hwy., Slidell, La. 70460

[21] Appl. No.: 360,257

[22] Filed: Jun. 2, 1989

[51] Int. Cl.$^5$ .............................................. A61B 1/32
[52] U.S. Cl. .............................. 128/17; 128/DIG. 26
[58] Field of Search ..................... 128/17, 11, 18, 912, 128/303.1, DIG. 26, 345; 604/180

[56] References Cited

U.S. PATENT DOCUMENTS

| | | | |
|---|---|---|---|
| 2,483,233 | 9/1949 | Price | 128/345 |
| 2,672,859 | 3/1954 | Jones | 128/77 |
| 3,029,303 | 4/1962 | Severino | 128/DIG. 26 |
| 3,368,564 | 2/1968 | Selix | 604/180 |
| 3,713,448 | 1/1973 | Arrott | 128/DIG. 26 |
| 3,977,407 | 8/1976 | Coleman et al. | 128/DIG. 26 |
| 4,074,397 | 2/1978 | Rosin | 128/DIG. 26 |

Primary Examiner—Edward M. Coven
Assistant Examiner—Mark S. Graham
Attorney, Agent, or Firm—Pravel, Gambrell, Hewitt, Kimball & Krieger

[57] ABSTRACT

A cervical speculum of the type having a first upper blade and a second lower blade, the blades movable in relation to one another via a rare hinge portion, and having the ability to be adjustable and used in conjunction with the gynecological procedure of, for example, surgery on the cervix. The improvement would include a pair of evacuator tubes which would be adaptable to the interior surfaces of the upper and lower blades respectively, each of the tubes having an adhesive material on that portion of the tube that would make adhesive contact with the surfaces of the upper and lower blades, with the tubes extending with their open ends at the ends of each of the blade portions, and extending rearwardly to the ends of the blades that are hingedly attached. Each of the tubes would lead into an evacuator tube, leading into an evacuator trap or line, so that the trap may be connected to a "stackhouse" filter which is the source of suction to evacuate the smoke and fluid from the patient's vaginal cavity during surgery. There may be further included a trap means so that the heavier liquids are contained in the trap, and the smoke from the laser surgery would be evacuated into the "stackhouse" filter for removal. The entire unit would be easily adaptable to an exisiting cervical speculum in order to allow use of existing speculums for this particular procedure.

5 Claims, 3 Drawing Sheets

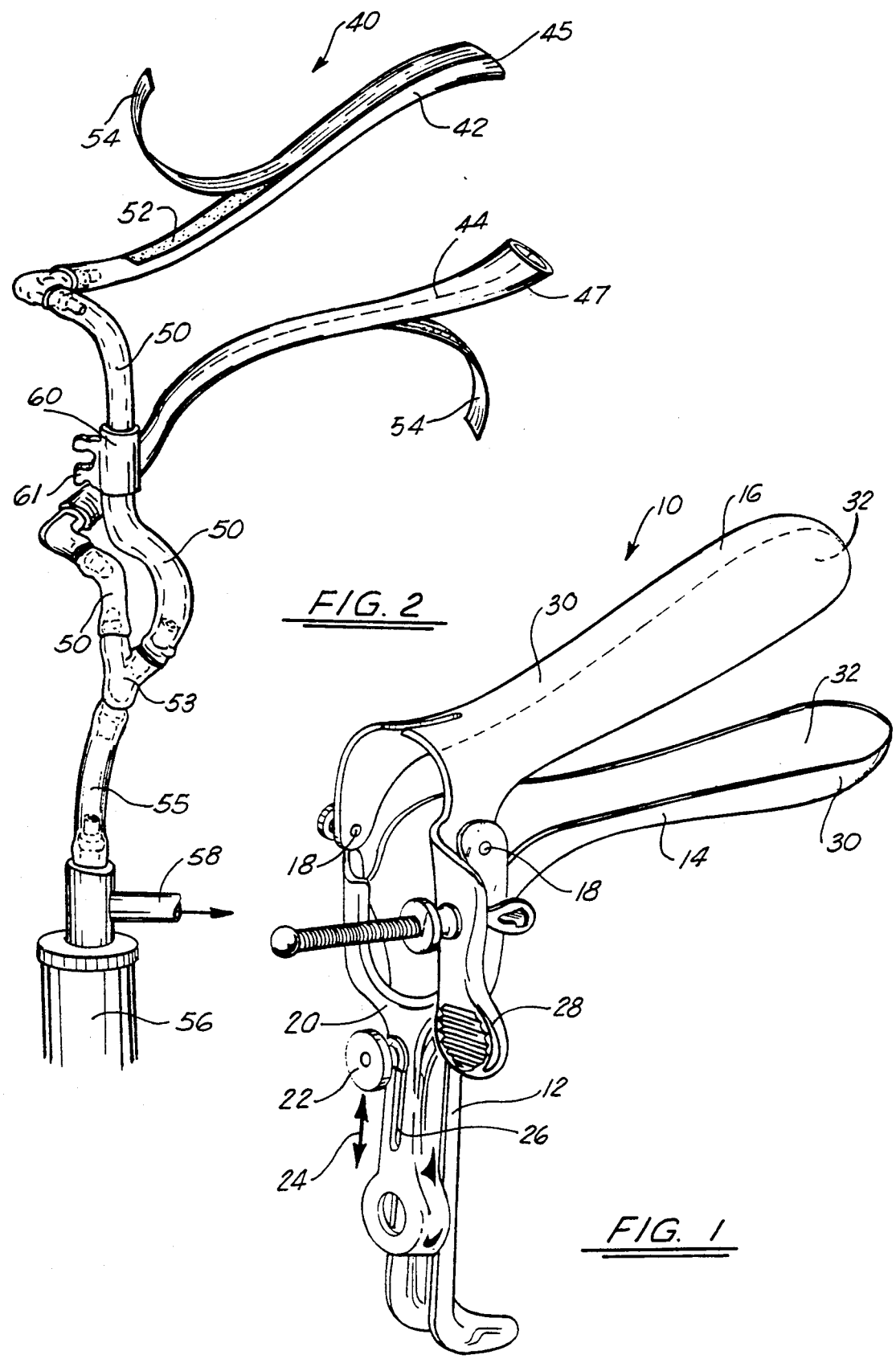

ADAPTER FOR CERVICAL SPECULUM

BACKGROUND OF THE INVENTION

1. Field of the Invention

The apparatus of the present invention relates to cervical speculums. More particularly, the present invention relates to an adapter and evacuation tube system which may be adapted to an existing cervical speculum, for drawing off excess fluid and smoke from a patient undergoing laser surgery in the treatment of vaginal related disorders.

2. General Background

In the therapy and treatment of disorders of the cervix, there is a developing technique chosen for outpatient therapy which is safe, and produces adequate cure-aids and is relatively inexpensive. The vast majority of vaginal intraepithelial neoplasia (CIN), lesions discovered in 80% of women screened for vaginal cancer or early small lesions located on the exposed portion of the cervix, may be managed on an out-patient basis. Although cryatherapy is a state of the art technique in the treatment of such pathology, in recent years, the carbon dioxide laser has gained in popularity in both private and institutional practices. It has been claimed that laser therapy for CIN yields higher cure rates and faster healing than cyrotherapy in that the squamocolumnar junction retains its location at the external OS following treatment. In addition, therapeutic success in the art of 95% after a single treatment and 99% after two lasers treatments have been reported.

One of the concerns in the treatment of vaginal condition through laser therapy is the problem surrounding the surgeons ability to properly perform laser surgery on the cervix due to the resultant stream of smoke that is emitted when the laser makes contact with human cells. This stream of smoke on one hand reduces a surgeon's ability to see properly the surgery being undertaken with the laser, and, on the other hand subjects the surgeon and surgical staff to cell fragments contained within the smoke or fluids which could be detrimental to the surgeon during such a technique.

As in all surgeries on the cervix, an instrument known as a speculum is utilized to increase the opening of the vagina so that the surgeon has relatively easy access to the area being treated. In fact, there are known speculums which do contain a tube attached to the blade of a speculum for either blowing air upon or siphoning off smoke that may be a result of electrical conization or cauterization upon the cervix, in order to overcome the presence of smoke in the vagina.

In view of the fact that most of the cervical speculums which are out on the market and being used, do not include any means for evacuating smoke or fluid during vaginal laser surgery, there is a need to provide a means whereby a surgeon may easily adapt a means for easily evacuating the smoke and fluid during the surgery, without having to discard the state of the art speculums which are presently being used by most if not all physicians during this type of medical treatment. In order to solve this problem, this speculum adapter has been devised for use under those particular circumstances. Several patents regarding speculums have been noted in the art, the most pertinent being as follows:

U.S. Pat. No. 2,483,233 issued to Price, et al, entitled "Speculum", relates to a speculum having a tube running in the upper jaw portion for blowing air into or for suctioning off smoke from the vagina following conization or cauterization upon the cervix.

U.S. Pat. No. 2,243,285, issued to Pope, entitled "Operating Scope", which is adapted for positioning of instruments therewithin, the scope adapted with a light source within the walls of the barrel for aspirating fluids therefrom.

U.S. Pat. No. 3,037,505, issued to Walden, entitled "Irrigators Or Spray Devices", relates to a spray device for distribution and injection of medication and cleaning preparations antibody cavities. The invention includes a spray tube which is readily detachable secured to a speculum but the second end of the tube may be coupled to a spring container.

U.S. Pat. No. 3,830,225, issued to Shinnick, entitled "Multi-Purpose Stop Cock Arrangement For Sucking Injection Oxygen Cessory Equipment", relates to a bronchoscope which allows the introduction or removal of fluid or instruments or both without withdrawing the other equipment from the bronchoscope.

Other art pertinent to the present invention is the Stack House Abdominal Smoke Control Valve which is a release system and valve that enables the laser surgeon to evacuate smoke from the inflated abdominal cavity during laser laparoscopy. The apparatus is manufactured and sold by Stack House Associates, Inc., which provides a filtration unit for the by-products from laser surgery of smoke and odor vaporized tissue through the use of a vacuum tube into the area of the laser. Such a filter would be used in conjunction with the present invention.

Applicant has presently pending entitled "Surgical Speculum", bearing Ser. No. 128,635, filed Dec. 4, 1987, now U.S. Pat. No. 4,884,559, which discloses a modified cervical speculum having upper and lower blades, the blades movable in relation to one another, the lower blade provided with a liquid evacuator tube built into the blade portion itself, with the top plate having a smoke evacuator tube for evacuating smoke from the patient. The tubes would end on their distal end and enter a trap in the handle portion with the speculum to evacuate the liquid and the smoke after surgery. The invention as disclosed in the present application would introduce a significant modification to that as disclosed in the earlier application, which provides for the adaptation of the filtration unit onto an existing cervical speculum.

SUMMARY OF THE PRESENT INVENTION

The apparatus of the present invention solves the problems confronted in the art in a simple and straightforward manner. What is provided is a cervical speculum of the type having a first upper blade and a second lower blade, the blades movable in relation to one another via a rare hinge portion, and having the ability to be adjustable and used in conjunction with the gynecological procedure of, for example, surgery on the cervix. The improvement would include a pair of evacuator tubes which would be adaptable to the interior surfaces of the upper and lower blades respectively, each of the tubes having an adhesive material on that portion of the tube that would make adhesive contact with the surfaces of the upper and lower blades, with the tubes extending with their open ends at the ends of each of the blade portions, and extending rearwardly to the ends of the blades that are hingedly attached. Each of the tubes would lead into an evacuator tube, leading into an evacuator trap or line, so that the trap may be connected to a "stackhouse" filter which is the source of suction to evacuate the smoke and fluid from the patient's vaginal cavity during surgery. There may be further included a trap means so that the heavier liquids are contained in the trap, and the smoke from the laser surgery would be evacuated into the "stackhouse" filter for removal. The entire unit would be easily adaptable to an existing cervical speculum in order to allow use of existing speculums for this particular procedure.

Therefore, it is the principal object of the present invention to provide a fluid adapter onto existing cervical speculums, to allow for the evacuation of fluids and smoke from the vagina during laser surgery.

It is still a further object of the present invention to provide an adapter which would be adhesively attached to the upper and lower blades of an existing cervical speculum, with the evacuator tubes evacuating smoke and fluid into a trap member, with the smoke being sucked into a suction pump during the process.

It is still a further object of the present invention to provide a separate evacuator attachment, which may be constructed of plastic or the like, that can be easily adhesively attached to an existing cervical speculum, so that the cervical speculum can be used during laser surgery without the need for a specialized speculum for that purpose.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is an overall isometric view of an existing typical cervical speculum;

FIG. 2 is an overall view of the evacuator adapter which would be adapted to the existing speculum in FIG. 1;

DETAILED DESCRIPTION OF THE PREFERRED EMBODIMENT

Figure 3:
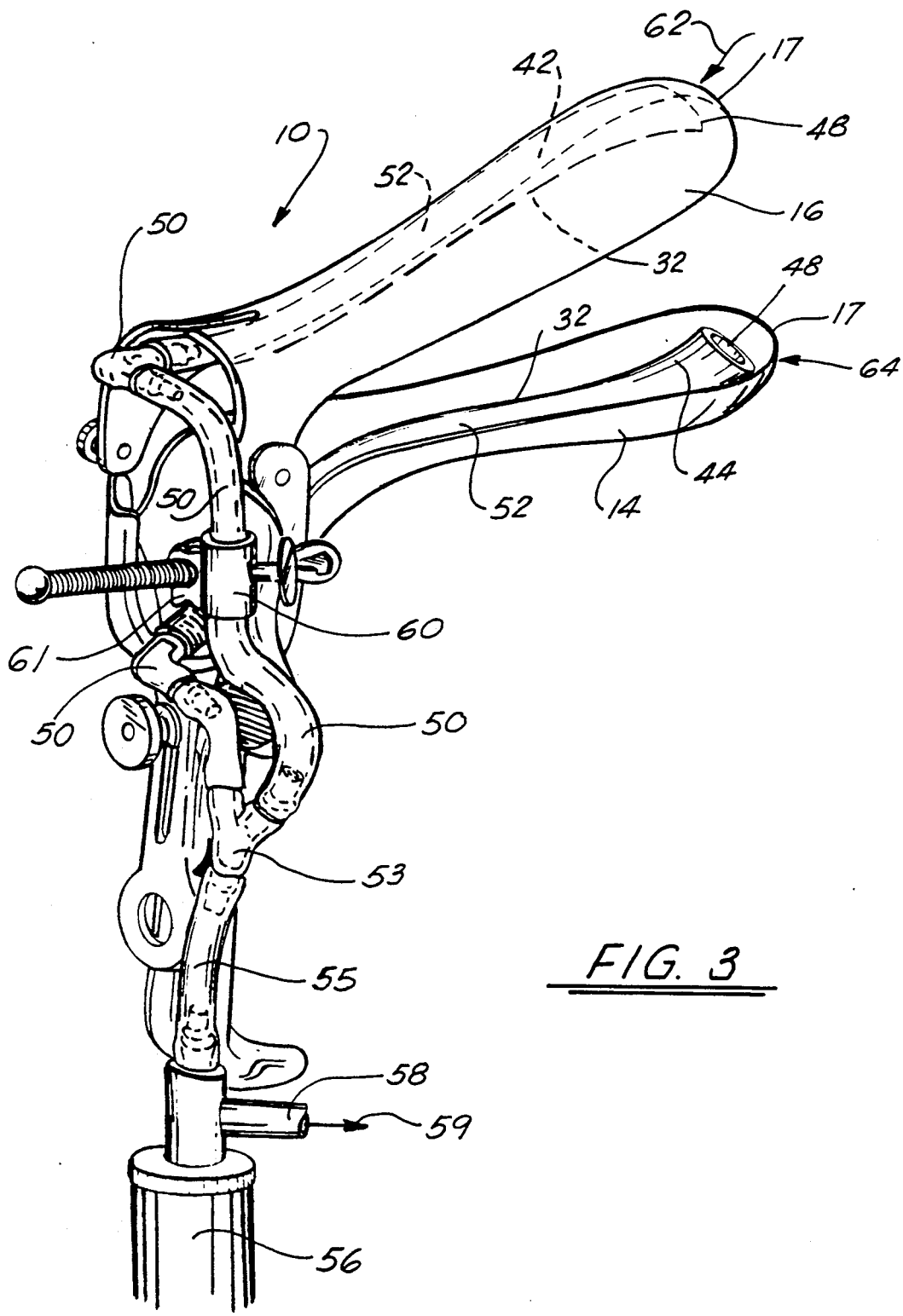
FIG. 3 is an overall view of the evacuator system adapted to the existing cervical speculum.
Figure 4:
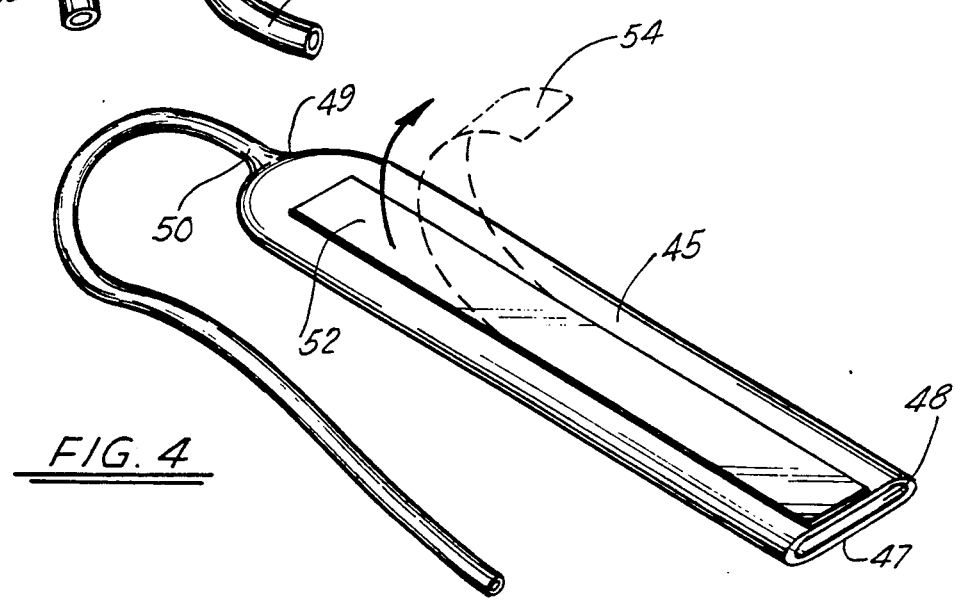
FIG. 4 is a detail view of one of the evacuator tubes utilized in the preferred embodiment of the adapter of the present invention.

FIGS. 2-4 illustrate the preferred embodiment of the adapter of the present invention, with FIG. 1 illustrating existing cervical speculum as identified by the numeral 10.

As illustrated in FIG. 1, speculum 10 would be a typical cervical speculum of the type having a handle portion 12, a rigid lower jaw member 14 integrally attached to and leading from handle portion 12, and a pivotally supported upward jaw member 16, mounted upon a bearing pin 18 at the upper end of handle portion 12, so that the upper jaw 16 is movable between open and closed positions in relation to the fixed jaw 14. In operation, the speculum is used in the normal manner and the jaw 16 is opened away from the fixed jaw 14 to hold the walls of the vagina properly delated during laser surgery. Furthermore, there is illustrated an adjustment member 20, which is fixed against the handle 12 via a screw 22, so that the relative opening between the end portions of blade members 14, 16 may be adjusted as the adjusting member 20 would move in the direction of arrow 24 as pin member would move within slot 26, to allow the blade members 14, 16 to move away from one another during use of the speculum. Furthermore, there is illustrated a standard thumb handle 28, for effecting the upward and lower movement of upper blade 16 during use of the speculum. It should be noted that blade members 14, 16 are in effect identical in that each of the blade members have an outer convex surface 30 and an inner concave surface 32, for defining a space within the concave surface 32 as illustrated in FIG. 1.

Figure 5:
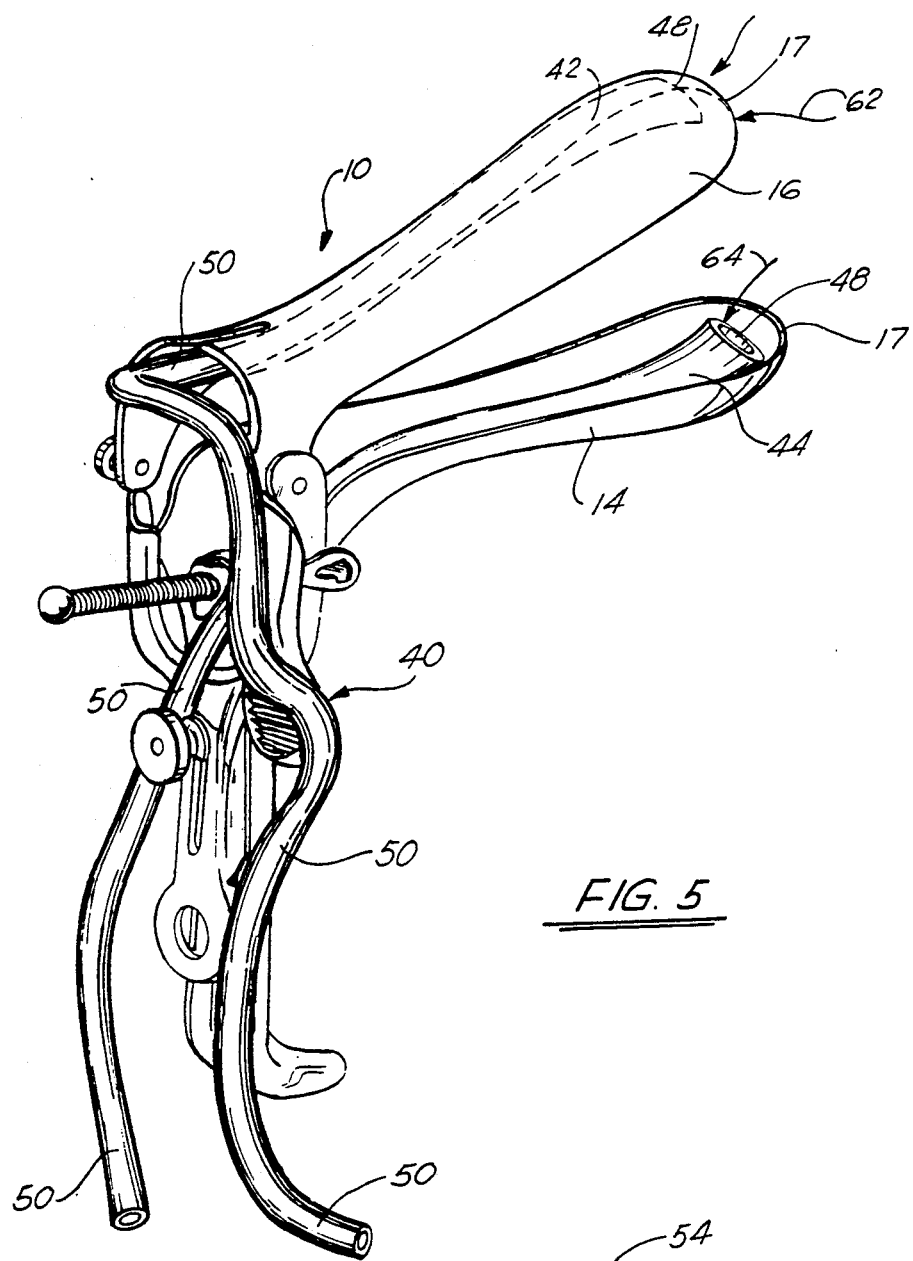
FIG. 5 is an overall view of an additional embodiment of the cervical speculum adapter of the present invention.

Turning now to the FIGURES which illustrate the adapter of the present invention. Reference is made to FIG. 2 which illustrates the adapter 40 of the present invention. Adapter 40 would include a first upper evacuator tube 42 and a second lower evacuator tube 44. Turning to FIG. 5, each of the evacuator tubes may be constructed so as to have an upper flattened surface 45 and a lower flattened surface 47, the flattened surfaces 45 and 47 forming an elongated opening 48 throughout the length of tubes 42, 44 for defining an evacuator space therewithin. The rear end portion 49 of each of the tubes 42, 44 would lead into an evacuator tube 50, evacuator tube 50 leading away from evacuator portions 42, 44 for evacuating fluids therefrom. As seen further in the FIGURES, each of the evacuator members 42, 44 would be equipped with an adhesive strip 52 positioned on the upper surface 45 of the upper tube 42, and on the lower surface 47 of the lower tube 44. The material may be a type of adhesive that may be covered with a strip 54 when the adapter is not in use, so that strip 54 may be peeled away from the adhesive 52 when the adapter is ready to be positioned onto the speculum blades 14, 16.

Prior to a discussion of that operation, reference is made again is made to FIG. 2, wherein each of the evacuator members 42, 44 as was stated earlier lead to an evacuator tube 50, with the evacuator tubes 50 leading into a Y 53, with Y 53 joining the tubes 50 to a common tube 55. Common tube 55 would then allow the passage of the vaginal fluids and the smoke produced by the laser surgery to be evacuated from common tube 55 into a trap 56 wherein the fluids would be contained. As noted, tube 54 would have an evacuation line 58 leading therefrom, with line 58 attached to a filter pump (such as a "stackhouse" filter), which is known in the art and therefore not illustrated, which serves as a means for suctioning off the smoke and fluids during the laser surgery. As further noted, one tube 50 would be adapted with a clip 60, the clip 60 being utilized to attach onto the speculum as will be illustrated further.

Turning now to FIG. 3, which illustrates the evacuator means 40 secured to the speculum 10 for use with the present invention. As illustrated, the upper tube 42 (phantom view) is illustrated as being adhesively secured to the interior surface 32 of upper blade member 16 after the adhesive strip 54 has been pealed from the adhesive material and secured along its length as illustrated, with the elongated opening 48 in the tube ending adjacent the very end 17 of upper blade 16, with the evacuator tube 42 extending into evacuator tube 50 as illustrated. For purposes of use of evacuator tube, when the "stackhouse filter", as activated, would be utilized to pull smoke in the area of the end 17 of upper blade 16 into the opening 48 of member 42, the smoke being identified by arrows 62 in FIG. 3. Next, and in the same manner, lower tube 44 would likewise have an adhesive strip 52 on its lower face 47 and after the protective layer 54 is peeled away from the adhesive strip 52, tube 44 would likewise be adhesively attached to the interior surface 32 of lower blade member 14, so that elongated opening 48 of tube 44 would be likewise positioned at the end 17 of tube 14, with tube 44 evacuating fluid likewise into line 50 for evacuation. Tube 44 would be used primarily to evacuate fluids or the like as identified by arrow 64 from the vagina through the lower tube 44 in view of the fact that the heavier liquids would tend to move to the bottom of the vagina where the tube 44 would then evacuate the fluids.

As illustrated again in FIG. 2, the line 50 would merge into a common line 54 where the fluids and smoke would then enter trap 56 with smoke being removed via line 58 into the "stackhouse filter" in the direction of arrow 59 and fluids would then be contained within trap 56 to be disposed of at a convenient time. As further illustrated in FIG. 3, the tube 50 leading from the upper chamber 42, would be engaged via clip means 61 by clamp 60 onto speculum 10, so that the tube would be secured in position other than with the adhesive layers 52. Furthermore, at the lower end, the trap member 56 could likewise be secured onto the handle portion 12 of the speculum 10, so as to have it more positively secured.

Turning now to FIG. 5, which is an additional embodiment, as noted, upper line 50 would simply lead from the upper chamber 42 and could be attached to a separate suction means for the smoke to be suctioned off. Likewise lower line 44 would be connected to line 50 independently from lower line 50, which would likewise be attached to a separate suctioning means. This embodiment would allow that, rather than the use of trap 56, one could simply plug each of the lines 50 into a separate suctioning unit for suctioning off the liquids and the smoke into different areas.

For purposes of construction, it is foreseen that apparatus 40 would be packaged totally independently of any speculum, and a physician may simply take the packaged adapter 40, remove the adhesive protector strips 54 and within a matter of minutes, could have a typical speculum 10, as illustrated in FIG. 1, adapted to be an evacuator speculum for use for laser surgery as seen in FIGS. 3 and 5. This quick adaption of an existing speculum would therefor allow a completely new use for such a speculum, with an adaption of evacuator 40 to an easy and quick adaptation.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An adapter for a vaginal speculum, having an upper blade member, a lower blade member in substantial parallel relationship with the other blade member and a handle member such that the upper and lower blade members move between open and closed positions relative to one another, the adapter comprising:
   (a) a first upper evacuator tube comprising an adhesive means on an outer surface of said first tube for attaching said tube to an under surface of the upper blade member;
   (b) a second lower evacuator tube comprising an adhesive means on an outer surface of said second tube for attaching said tube to an under surface of the lower blade member, each of the first and second evacuator tubes having a first open end portion locatable at a distal end of each of the blade members respectively;
   (c) means for establishing a suction within each of the upper and lower tubes, for drawing fluids into the ends of the upper and lower tubes, so that the fluids can be evacuated from the vaginal area during laser surgery, and
   means for securing the adapter to the speculum in addition to the adhesive means on the upper and lower tube members.

2. The adapter in claim 1, further comprising a trap means at a second end portion of the upper and lower tubes, for trapping any liquids suctioned through the tubes.

3. The adapter in claim 1, wherein the tubes are adhesively attachable to the upper and lower blade members via a length of adhesive material along the outer wall of the upper and lower tubes.

4. The apparatus in claim 1, wherein the adapter further comprises means for suctioning smoke out of the trap means during the evacuation process.

5. An adapter for use with a vaginal speculum, the speculum having a first upper blade member and a second lower blade member operable in parallel relation to the upper blade member, the upper and lower blade members including concave interior surfaces, each blade member having a distal end portion, a handle member attached to the blade members, the upper blade member movable in relation to the lower blade member between open and closed positions, the adapter comprising:
   (a) a first upper evacuator tube, having an open ended distal end portion adjacent the distal end portion of the upper blade member, and having a length of adhesive along its upper surface, the adhesive including a removable strip, sot hat the adhesive may be exposed to the concave surface of the upper blade member and can be secured thereto;
   (b) a second lower evacuator tube having an open ended distal end portion adjacent the distal end portion of the lower blade member, and having a strip of adhesive on its lower surface, and a strip which may be peeled away so that the adhesive may be exposed to the exterior surface of the lower blade member and can be secured thereto;
   (c) suction means, attached to an opposite end portion of the upper and lower tube, for suctioning off fluid during laser surgery; and
   (f) trap means at the opposite end of the tubes for trapping liquids evacuated through the upper and lower tubes during laser surgery.

* * * * *